US008987686B2

(12) United States Patent
Rizkallah et al.

(10) Patent No.: US 8,987,686 B2
(45) Date of Patent: Mar. 24, 2015

(54) METHOD AND SPECTROSCOPIC ANALYSIS APPLIANCE, ESPECIALLY FOR ANALYSING FOOD, WITH MULTI-CHANNEL TREATMENT OF SPECTRAL DATA

(75) Inventors: Jad Rizkallah, Beirut (LB); Inès Birlouez-Aragon, Ermont (FR)

(73) Assignee: Spectralys Innovation, Romainville (FR)

( * ) Notice: Subject to any disclaimer, the term of this patent is extended or adjusted under 35 U.S.C. 154(b) by 395 days.

(21) Appl. No.: 13/516,358

(22) PCT Filed: Dec. 8, 2010

(86) PCT No.: PCT/FR2010/000826
§ 371 (c)(1),
(2), (4) Date: Jul. 26, 2012

(87) PCT Pub. No.: WO2011/080408
PCT Pub. Date: Jul. 7, 2011

(65) Prior Publication Data
US 2012/0280146 A1 Nov. 8, 2012

(30) Foreign Application Priority Data

Dec. 16, 2009 (FR) .................................... 09 06088
Mar. 26, 2010 (FR) .................................... 10 01221

(51) Int. Cl.
*G01N 21/64* (2006.01)
*G01N 33/02* (2006.01)
(52) U.S. Cl.
CPC ................ *G01N 21/64* (2013.01); *G01N 33/02* (2013.01); *G01N 2021/6419* (2013.01); *G01N 2201/129* (2013.01)
USPC ..................................................... 250/459.1

(58) Field of Classification Search
CPC ....................... G01N 2021/6419; G01N 33/02
USPC ............................................................. 250/459.1
See application file for complete search history.

(56) References Cited

U.S. PATENT DOCUMENTS

| 5,151,748 A | * | 9/1992 | Bur et al. ......................... 356/32 |
| 7,236,815 B2 | * | 6/2007 | Richards-Kortum et al. 600/407 |
| 7,569,839 B2 | * | 8/2009 | Gilmore et al. ............ 250/459.1 |

FOREIGN PATENT DOCUMENTS

WO WO 2008/012706 A2 1/2008

OTHER PUBLICATIONS

Christensen, J. et al., *Fluorescence Spectroscopy and PARAFAC in the Analysis of Yogurt*, Chemometrics and Intelligent Laboratory Systems 75 (2005) 2001-2008.
(Continued)

*Primary Examiner* — Kiho Kim
(74) *Attorney, Agent, or Firm* — Alston & Bird LLP (57) ABSTRACT

A method for the spectroscopic analysis of a sample is provided. The method including the illumination of the sample to be analyzed by a plurality of luminous excitation rays with respective wavelengths; the acquisition and the pre-treatment of frontal fluorescence spectra, each spectrum corresponding to a respective luminous excitation ray; for each sample, the calculation of a score vector by applying a multi-channel statistical model to the pre-treated spectra; and the determination of at least one parameter selected from a quality indicator of the sample and a parameter characterizing a method that has been applied to the sample, from said score vector. The average spectral distance between the luminous excitation rays is at least 50 nm, over a spectral range of at least 100 nm. The invention also relates to an appliance for implementing such a method.

18 Claims, 4 Drawing Sheets

(56) References Cited

OTHER PUBLICATIONS

Nahorniak, M. L. et al., *Optimizing the Implementation of the PARAFAC Method for Near-Real Time Calibration of Excitation-Emission Fluorescence Analysis*, Journal of Chemometrics, 17 (2003) 608-617.

International Search Report and Written Opinion for Application No. PCT/FR2010/000826 dated Feb. 6, 2012.

Bro, R., *Multi-Way Analysis in the Food Industry Models, Algorithms, and Applications*, PhD Thesis, Universiteit Van Amsterdam, 1998.

Davidson, R. et al., Econometric Theory and Methods, Generalized Least Squares and Related Methods, *Econometric Theory and Methods*, Oxford University Press (2004) 255-261.

Dhanoa, M. S. et al., *The Link Between Multiplicative Scatter Correction (MSC) and Standard Normal Variate (SNV) Transformations of NIR Spectra*, J. Near Infrared Spectrosc., 2 (1994) 43-47.

Harshman, R. A., *How Can I Know If It's Real? A Catalog of Diagnostics to Use With Three-Mode Factor Analysis and Multidimensional Scaling*, In: Research Methods for Multimode Data Analysis, Law et al., eds., Praeger, New York, (1994) 566-571.

Rizkallah, J., *Chemometric Analysis of Front Face Florescence Data—Estimation, of Neoformed Contaminants in Processed Foods*, PhD Thesis, Argo Paris Tech France (2007).

Rizkallah, J. et al., Front Face Florescence to Monitor Food Processing and Neoformed Contamination, *Optical Methods for Monitoring Fresh and Processed Food—Basics and Applications for a Better Understanding of Non-Destructive Sensing*, Chapter 4, Editor M. Zude Publisher CRC Press, USA (2008).

Wold, S. et al., *Orthogonal Signal Correction of Near-Infrared Spectra*, Chemometr. Intell. Lab. Syst. 44 (1998) 175-185.

\* cited by examiner

METHOD AND SPECTROSCOPIC ANALYSIS APPLIANCE, ESPECIALLY FOR ANALYSING FOOD, WITH MULTI-CHANNEL TREATMENT OF SPECTRAL DATA

CROSS-REFERENCE TO RELATED APPLICATION

This application is a national stage application filed under 35 U.S.C. 371 of International Application No. PCT/FR2010/000826, filed Dec. 8, 2010, which claims priority from French Application No. 0906088, filed Dec. 16, 2009 and French Application No. 1001221, filed Mar. 26, 2010, each of which is incorporated by reference herein in its entirety.

FIELD

The invention relates to a method and an appliance for spectroscopic analysis of at least one sample, in particular of a food or drug, implementing a method for analyzing spectroscopic data based on a multi-way statistical model. The invention can be used in particular, but not exclusively, in the study of the change in nutritional properties (vitamin content, etc.) and/or toxicological properties (neoformed contaminant content, etc.) of a food during its preparation or preservation. More generally, the invention can be used in the determination of any quality indicator of a sample, and/or any parameter characterizing a method to which said sample has been subjected.

BACKGROUND

Neoformed contaminants (NFC) are new molecules formed in a food based on components specific to said food, due to the action of transformation methods, and which present public health problems. Few public or private laboratories are capable today of assaying these contaminants. Moreover, even if numerous methods have been published for the assay of each of the contaminants, none of them has really been the subject of standardization and normalization. In addition, these analyses are costly and the time period for obtaining results is long (2 to 3 weeks). The industry requires faster and less expensive analysis methods to ensure control of conformity of its methods and the safety of the foods that it produces.

Food transformation methods (cooking, sterilization, preservation) can also have an unfavorable influence on the nutritional properties of foods, for example by reducing their vitamin content. The characterization of these methods and their influence on the nutritional properties of foods presents problems similar to those, mentioned above, of assaying neoformed contaminants.

The use of analyses, in particular spectroscopic, of foods using the methods of chemometry, and in particular multi-way analysis, is known.

Multi-way analysis is the natural extension of multivariate analysis when the data is arranged in three-way or more-than-three-way tables. It is based on the use of statistical models such as "PARAFAC" ("Parallel Factor") and NPLS ("N-ways Partial Least Squares regression"). These methods, as well as their use in the analysis of food products, are described in the document [Bro 1998].

More specifically, [Rizkallah 2007] describes a method for analyzing unprepared samples (only ground, if necessary) based on the use of the PARAFAC model with front-face fluorescence spectra. This method involves the illumination of a sample by a plurality of monochromatic light radiations with respective wavelengths, and the acquisition of corresponding fluorescence spectra. The excitation radiation will finely sample (at several hundred points) a spectral range covering the visible and the near-UV; in turn, the fluorescence emission spectra are spectrally sampled (also at several hundred points). The spectral data thus collected for each sample is arranged in a large matrix called an "excitation-emission matrix" (EEM), of which one dimension represents the emission wavelengths and the other dimension represents the emission wavelengths.

The EEMs corresponding to a plurality of calibration samples are analyzed by the PARAFAC method, which makes it possible to extract information, called "PARAFAC factors", which correspond to the bi-linear fluorescent profiles and to their relative intensities. Then, a multiple regression between the fluorescent intensities and the neoformed contaminant content (or content of other substances of interest) chemically measured makes it possible to construct a calibration model that is then used to predict the content of neoformed contaminants on the basis of the EEMs collected on new samples to be analyzed.

This method has two major limitations:

First, it requires high-cost equipment: a spectrofluorometer equipped with a Xenon lamp delivering all of the wavelengths from the near-UV to the visible, and two monochromators capable of transmitting these different excitation and emission for the photons emitted by the sample.

Second, its implementation is time-consuming because, even if the preparation of the sample is not necessary, the acquisition of each EEM takes 15 to 45 minutes according to the desired spectral resolution. The analysis of these data matrices, including a considerable number of variables, is also onerous in spite of the automation of data processing algorithms.

A similar method is described by [Rizkallah et al., 2008].

The document [Nahorniak 2003] studies the influence of spectral resolution (and therefore the size of the EEM matrix) on the prediction error of a fluorophore by applying the PARAFAC method. In this document, diluted solutions with a simple and known composition are considered; in addition, all of the measurements are performed with a high spectral resolution, of 2 nm/pixel, and the reduction in resolution is obtained by calculating spectral averages.

This study finds that the prediction error is minimized—and is around 0.5 to 1%—for an excitation resolution of 6 to 10 nm/pixel, then increases significantly for lower resolutions (increase by a factor of 2 to 6, reaching a resolution of 20 nm/pixel). It therefore appears to be difficult to use resolutions below 20 nm/pixel.

SUMMARY

The invention is intended to provide a simpler, faster analysis method requiring simple and less expensive equipment, and therefore more suitable for industrial requirements.

According to the invention, such an objective is achieved by a method for spectroscopic analysis of at least one sample implementing a method for analysis of spectroscopic data based on a multi-way statistical model, which method includes:

a) the illumination of said or of each sample to be analyzed by a plurality of excitation light radiations with respective wavelengths;

b) the acquisition of front-face fluorescence spectra of said or of each sample, each corresponding to a respective excitation light radiation;

c) a pre-processing of the fluorescence spectra acquired;

d) for each sample, the calculation of a score (or light intensity) vector by application to the pre-processed spectra of said multi-way statistical model, identified by a fluorescence excitation loading (or spectrum) vector and by an emission loading (or spectrum) vector; and
e) the determination of at least one parameter chosen from a quality indicator of said or of each sample and a parameter characterizing a method to which said or each sample has been subjected, on the basis of said score vector;
the method being characterized in that the average spectral gap between said excitation light radiations is at least 20 nm (preferably at least 50 nm) over a spectral range of at least 100 nm.

Advantageously, the number of excitation light radiations and corresponding fluorescence spectra for each sample can be between two and six, and preferably between three and five, over a spectral range of at least 100 nm, and preferably of at least 150 nm.

This method is innovative because it uses multi-way analysis tools such as the PARAFAC model, normally used for large EEMs, in an assembly consisting of a limited number of spectra (generally two to six, and preferably between three and five), very roughly sampling the spectral excitation range of the samples. This range is relatively large (at least 100, and even 150 nm or more) because the physicochemical composition of said samples is largely unknown, and therefore the exact position of the absorption spectra of the fluorophores contained in said sample is as well.

The present inventors surprisingly discovered that the multi-way models continue to be applicable and provide results that can be used even with such a rough spectral excitation resolution, and such a limited number of excitation wavelengths.

It is important to emphasize that, from a physical perspective, the "loadings" represent the emission or excitation spectra of each factor, and the "scores" represent the intensities of said factors. A "PARAFAC factor" represents the contribution of a fluorophore, or a mixture of fluorophores, common to the samples analyzed. It is also necessary to emphasize that the fluorescence spectra are deformed by the interaction between the excitation photons and the emitted photons with the food matrix and that the condition of tri-linearity generally accepted for the application of the PARAFAC model is not satisfied. Nevertheless, the inventors have shown that this model is usefully applied to such EEM matrices in order to describe their fluorophore composition.

It is necessary to understand that the method of the invention is not (at least not necessarily) intended to determine the concentration of fluorophores themselves. This method simply uses correlations, generally non-linear or multi-linear, between the changes in the fluorescence excitation and emission spectra and certain quality parameters of the sample (concentration of nutrients and/or contaminants, which, usually, are not fluorescent; microbial load, etc.) or certain parameters characterizing a method to which said sample has been subjected (sterilizing, pasteurizing or cooking value, or a time-temperature product, for example).

A comparison with the aforementioned document [Nahorniak 2003] is particularly interesting. This document relates to a particularly favorable case, namely the analysis of solutions with a simple and known composition. By contrast, the invention relates to the front-face fluorescence analysis of complex and highly scattering samples, of which the composition is largely unknown. Moreover, in document [Nahorniak 2003], the spectra are acquired at a high spectral excitation resolution, then averaged, which is likely to reduce the prediction error. By contrast, in the case of the invention, only two to six spectra are acquired, with an extremely low spectral excitation resolution, below 20 nm/pixel and even 50 nm/pixel. In spite of this, a suitable choice of parameters for the multi-way model and/or a suitable pre-processing of the data make it possible to limit the prediction error to entirely acceptable values, typically below 15% or even 10%.

A method according to the invention can also include a preliminary calibration phase, comprising:
i) the illumination of a plurality of calibration samples by said excitation light radiation;
ii) the acquisition of front-face fluorescence spectra of the samples, corresponding to said excitation light radiation;
iii) a pre-processing of the acquired fluorescence spectra;
iv) the determination, by an iterative method, of said loading excitation and emission vectors of the multi-way model, as well as a score vector for each calibration sample; and
v) the determination of a regression function linking said scores to the known values of said or of each parameter for said calibration samples.

The fluorescence spectra can be self-fluorescence spectra or, in some cases, fluorescence spectra induced by a marker added to the sample. For example, the estimation of the microbial load of a sample can be largely facilitated by the use of a fluorescent probe.

Advantageously, the fluorescence spectra can be pre-processed by subtracting a contribution due to the first-order Rayleigh scattering of the excitation light radiation, with said contribution being calculated by means of a generalized linear model. In particular, said generalized linear model can be determined on the basis of a first portion of the spectrum to be pre-processed, including only said contribution due to the Rayleigh scattering, and is used to predict the Rayleigh scattering contribution in a second portion of said spectrum in which it is superimposed with a fluorescence contribution. The subtraction of the Rayleigh scattering is also necessary in the analysis methods known from the prior art, but becomes critical in the method of the invention. The use of a generalized linear model, instead of the known techniques of replacement with zeros or missing values, is particularly advantageous when a very small number of excitation wavelengths is used, as in the case of the invention.

Then, the fluorescence spectra can also be pre-processed by normalizing them. A plurality of samples, for calibration and/or analysis, can also be pre-processed by performing a multiplicative scatter correction.

According to a preferred embodiment of the invention, said multi-way statistical model can be a PARAFAC model, with the fluorescence spectra of each sample being represented in concatenated form. In this case, the loading vectors of said PARAFAC model can be determined by an iterative method that is stopped when the reduction of the loss function due to the last iteration goes below a threshold value ("convergence parameter") between $10^{-4}$ and $10^{-2}$. This value must be compared with that generally used, of $10^{-6}$. Indeed, the use of a larger convergence parameter facilitates the convergence of the PARAFAC model when a small number of excitation wavelengths is used.

Alternatively, said multi-way statistical model can be an NPLS model, with the fluorescence spectra of each sample being represented in concatenated form. In this case, the fluorescence spectra can usefully be pre-processed by orthogonal signal correction.

Advantageously, said excitation light radiation can include: a first radiation with a wavelength of between 270 and 300 nm; a second radiation with a wavelength of between 300 and 360 nm; and a third radiation with a wavelength of between 400 and 500 nm.

Said or at least one said parameter to be determined can be chosen, in particular, from: the concentration of a substance of interest in said or in each sample; a microbial load of said or of each sample; and a sterilizing, pasteurizing or cooking value, or a time-temperature product, of a method to which said or each sample has been subjected.

The concepts of sterilizing, pasteurizing or cooking value are well known by themselves. A step of a thermal method is considered, in which the sample is kept at a temperature $T_i$ (in °C., at the core of the sample) for a time $t_i$. The pasteurization value of this step is:

$$VP_i = t_i \times 10^{\frac{T_i - 70}{Z}}$$

its sterilizing value is:

$$VS_i = t_i \times 10^{\frac{T_i - 121.1}{Z}}$$

and its cooking value is:

$$VC_i = t_i \times 10^{\frac{T_i - 100}{Z}}$$

in which the parameter Z is dependent on the microorganism considered (for the pasteurizing and sterilizing values) or on the nature of the sample (for the cooking value).

For a multi-step method, the sum of the pasteurizing or sterilizing values of the different steps is taken.

The samples to be analyzed and for calibration can be, in particular, samples of a product chosen from a food and a drug.

The invention also relates to the use of a method as described above for measuring the change in nutritional, microbiological and/or toxicological properties of a food during its preparation or preservation.

The invention also relates to an appliance for spectroscopic analysis of at least one sample comprising: a set of light sources for illuminating said or each sample to be analyzed by respective excitation light radiations, having different wavelengths with an average spectral gap of at least 20 nm over a spectral range of at least 100 nm; means for acquisition of the front-face fluorescence spectra emitted by said or each sample when illuminated by said excitation light radiation; and means for processing the fluorescence spectra acquired, suitable for implementing a method as described above. Preferably, such an appliance can comprise between two and six (and preferably between three and five) of said light sources.

Advantageously, such an appliance can comprise: a first light source emitting radiation at a wavelength of between 270 and 300 nm; a second light source emitting radiation at a wavelength of between 300 and 360 nm; and a third light source emitting radiation at a wavelength of between 400 and 500 nm.

BRIEF DESCRIPTION OF THE DRAWINGS

Other features, details and advantages of the invention will become apparent in the following description, with reference to the appended drawings, provided as examples, and which show, respectively.

DETAILED DESCRIPTION

The method of the invention uses the fluorescence signal emitted at the surface of the food after illumination with light beams at predetermined wavelengths of the UV-visible domain (approximately: 250-750 nm). This signal is analyzed by chemometric methods making it possible to extract the information correlated with the parameters to be measured. The existence of such a correlation is deduced from the fact that, during agricultural production, preservation and transformation, the intrinsic fluorescence of the natural constituents of the food (vitamins, proteins and other natural or intentionally or unintentionally added constituents), as well as their reflectance, change, while, at the same time, new signals appear due to the formation of new molecules (including neoformed contaminants). We refer to neoformed or acquired fluorescence depending on whether the fluorophores are formed de novo or come from the environment. The joint change in native signals (NS), neoformed signals (NFS) and newly-acquired signals (NAS) is strongly correlated with the physical, physicochemical, chemical or microbiological modifications of the food, and in particular with changes in quality parameters, caused during production, preservation and/or transformation. The change factors that influence the quality of the food are oxidizing ultraviolet radiation, the destruction of microorganisms or, by contrast, the development of some microorganisms capable of leading to the synthesis of mycotoxins, human intervention in cultures (fertilizers, pesticides, etc.), or the use of methods modifying the temperature, pressure or any other physical parameter of the food and that consequently cause a modification in the physicochemical composition and quality parameters.

The excitation light radiation includes wavelengths chosen so as to explore the widest possible UV-visible spectrum. In general, it is possible to choose, a priori:
a wavelength of between 270 and 300 nm enabling the excitation of tryptophan, phenols such as chlorogenic acid or hydroxytyrosol or even vitamin E, molecules emitting in the UV;

a wavelength of between 400 and 450 or 500 nm enabling excitation of riboflavin, porphyrins and chlorophyll, molecules emitting in the visible (500-700 nm);

one or two wavelengths between 300 and 360 or even 400 nm are introduced so as to excite the neoformed fluorophores, essentially Maillard products and lipid peroxidation products, but also mycotoxins emitting in the far-near visible UV (400-500 nm).

These wavelengths will be modified in the case of applications other than in the food industry. In any case, for greater precision, it is possible to choose the wavelengths as close as possible to the maximum loadings representing the excitation vector obtained by the PARAFAC decomposition of a complete EEM matrix obtained with a laboratory fluorometer on a batch of representative samples.

The number of wavelengths used is between 2 and 6, advantageously between 3 and 5, and preferably equal to 5, enabling a corresponding number of fluorophore groups among those described above to be excited in turns. The intensity of the excitation radiation is chosen so that the fluorescence emission energy of these fluorophores is significantly modified during the transformation steps to be characterized. For example, the intensity must be high enough that the appearance of mycotoxins related to the development of fungi on a grain during its transformation will substantially modify the fluorescence emission collected on the detector based on an uncontaminated sample. It must also make it possible to demonstrate the use of such a heat treatment characterized by a time-temperature pair, or the use of washing, bleaching or decontamination treatment.

Figures 5, 6:
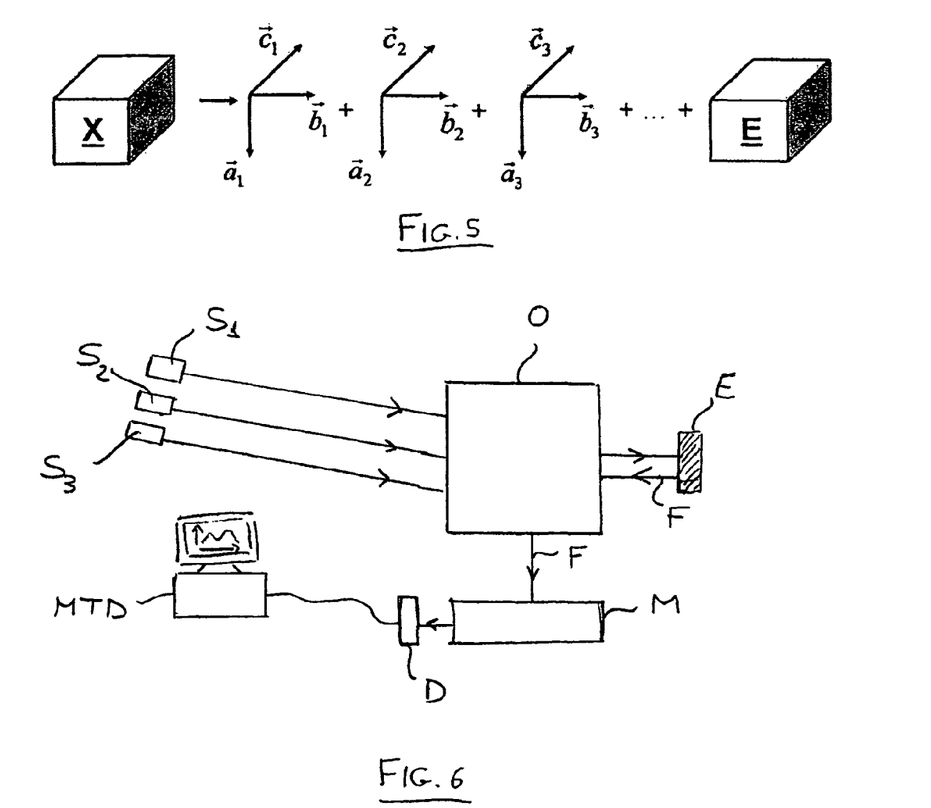
FIG. 5: a diagrammatic illustration of the PARAFAC method.
FIG. 6: the schematic layout of an analysis appliance according to an embodiment of the invention.

FIG. 6 shows a very simplified diagram of an appliance for implementing the method of the invention. This appliance includes three light sources $S_1$, $S_2$ and $S_3$ each emitting a monochromatic radiation beam at a different wavelength, directed so as to illuminate the sample E. The fluorescence signal F (in fact, a mixture of fluorescence and Rayleigh scattering of the first and sometimes second order) emitted by this sample is transported by an optical fiber to a spectrometer, which decomposes the light radiation emitted in the spectrum. The spectra acquired are processed by data processing means MTD (typically a suitably-programmed computer) making it possible to extract the desired chemometric information.

The light sources can typically be light-emitting diodes, or even lasers (preferably semiconductor) if high intensities are required.

The analysis of the spectroscopic data, performed by the data processing computer MTD, comprises four main steps:
the pre-processing of the spectra;
the determination of the "loading" vectors of the multi-way model by means of the spectra of the calibration samples;
the determination of the "score" vectors by applying this model to the spectra of the samples to be analyzed; and
the determination of chemical information (concentration of one or more substances of interest), physical information (time-temperature product, sterilizing, pasteurizing or cooking value), or physicochemical or microbiological information (microbial load) on the basis of said "score" vectors.

First, the pre-processing of the spectra is considered in reference to a specific example, in which a roasted chicory sample is illuminated successively by three excitation radiations at 280, 340 and 429 nm. Each of the three fluorescence spectra consists of 1515 spectral intensity values for as many different wavelengths λ. The spectral resolution is 0.25 nm/pixel, but it can be divided by 5 or even more, without any degradation of the results of the method of the invention being observed.

Figure 1:
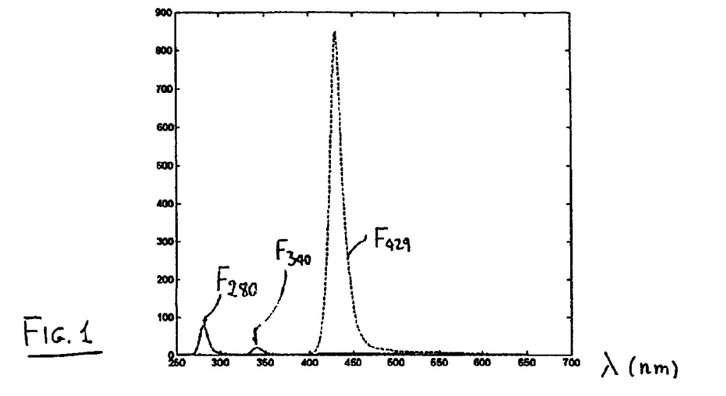
FIG. 1: three "raw" fluorescence spectra of a roasted chicory sample, corresponding to three excitation radiations at different wavelengths.
Figure 3A:
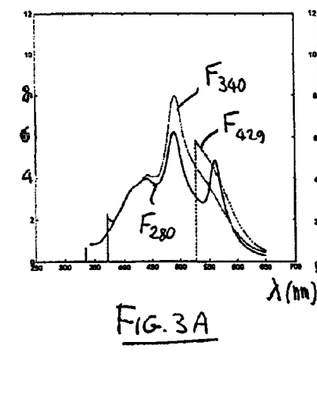
FIGS. 3A, 3B, 3C: three graphs comparing said Rayleigh scattering subtraction method (FIG. 3C) with two other methods known from the prior art: the replacement with zeros (FIG. 3A) and the replacement with missing values (FIG. 3B)
Figure 3B:
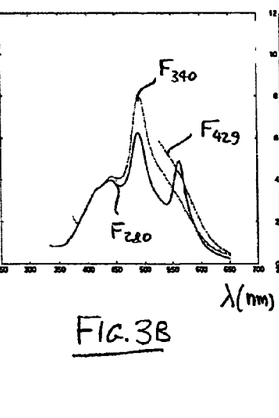
Figure 3C:
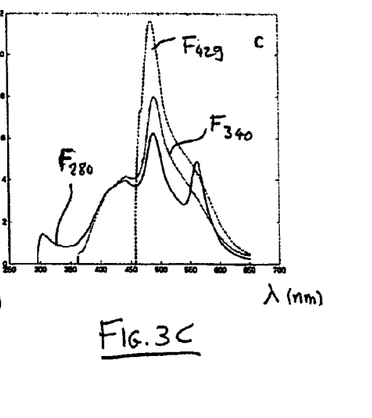

The "raw" spectra (FIG. 1) are dominated by the first-order Rayleigh scattering, at the excitation radiation wavelengths (280, 340 and 429 nm). The spectrum of each fluorescence signal, indeed, is partially superimposed with the scattered excitation radiation, which is much more intense. This problem is known, and is generally solved by replacing the intensity values corresponding to the spectral superimposition region with zeros (FIG. 3A) or missing values (FIG. 3B). In these figures, the references $F_{280}$, $F_{340}$ and $F_{429}$ represent the fluorescence spectra relating to the excitations at 280, 340 and 429 nm, respectively, in which the intensities of the spectral overlap regions with the Rayleigh scattering have been replaced by zeros or missing values.

These methods have disadvantages, because the replacement with zeros produces artifacts and therefore falsifies the analysis by creating artificial variances. The replacement with missing values produces convergence problems of the multi-way models used for the data analysis. Moreover, the presence of missing values prevents the use of standardization pre-processing operations (see below), which can be applied only to real values.

These problems are acceptable in the case of conventional techniques, based on the use of large EEMs, but easily become prohibitive in a method such as that of the invention, based on the analysis of data very easily solved by the excitation wavelength.

For this reason, the invention proposes eliminating the contribution of the first-order Rayleigh scattering by an innovative technique based on the prediction of the scattering region that overlaps the fluorescence via a generalized linear model (GLZ) with a log linking function [Davidson 1998; Rizkallah 2007]. This model is calibrated on a region of the spectrum in which the contribution of the fluorescence is negligible, and the spectral intensity is attributed exclusively to the scattering (reference RD in FIGS. 2A and 2B).

The generalized linear model has the form:

$$f(\mu_y) = b_0 + b_1 x$$

In the equation, $f(\mu_y)$ is the linking function of $\mu_y$, the expected value of y, with y being the vector of the Rayleigh scattering intensities that do not overlap with the fluorescence, while x is an index vector (1, 2, 3, etc.) of the same size as y.

With the generalized model, non-linear relations (between x and y) can be modeled via the linking function. The generalized model can be used to model dependent variables having distributions belonging to the exponential family (normal, gamma, Poisson, etc.). The multiple linear regression is a special case of the GLZ model that corresponds to a linking function equal to the identity function and to a dependent variable (y) having a normal distribution.

The $b_i$ parameters of the GLZ model are estimated by the statistical method for maximization of likelihood (L):

$$L = F(Y, \text{model}) = \Pi_{i=1}^n p[y_i, b_i]$$

in which $p[y_i, b_i]$ is the probability of $y_i$ dependent on $b_i$.

The objective is to find the parameters that give the greatest probability (joint density) of producing y for all observations. An iterative estimation (Fisher algorithm, which is a quasi-Newtonian method) is used to find the parameters $b_i$ by maximizing L:

$$\frac{\partial \log(L)}{\partial b_i} = 0$$

Figure 2A:
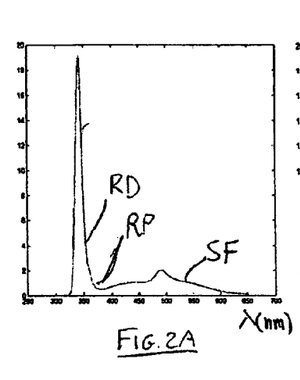
FIGS. 2A, 2B and 2C: three graphs showing the Rayleigh scattering subtraction operation by the method using a generalized linear model.
Figure 2B:
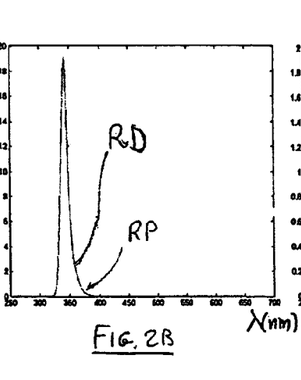
Figure 2C:
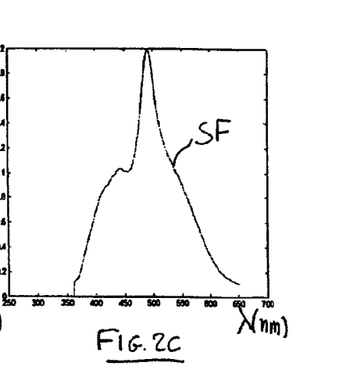

Once the $b_i$'s have been estimated, the GLZ model is applied to the scattering indices corresponding to the spectral region superimposed with the fluorescence (FIG. 2B—prediction region RP) in order to predict the "pure" scattering intensities. After this prediction, the complete scattering spectra (real and predicted parts) are subtracted from the EEMs to obtain the pure fluorescence spectrum SF (FIG. 2C—to be compared with FIG. 2A showing the fluorescence spectrum partially superimposed with the scattered light spectrum).

Figure 4:
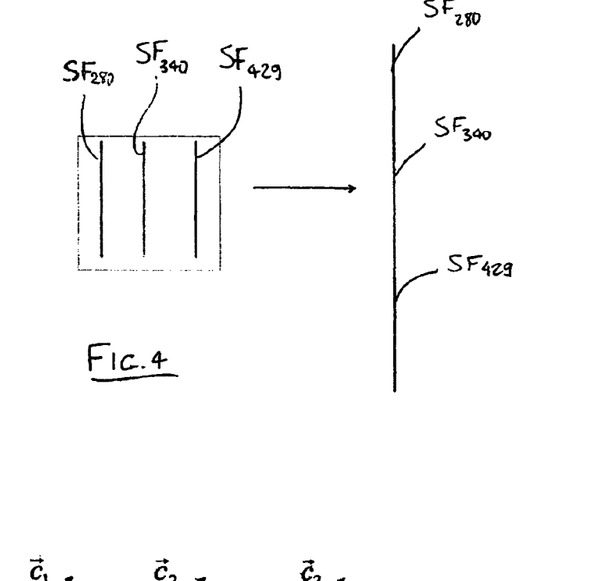
FIG. 4: a diagrammatic illustration of the concept of concatenation of spectra.

The successive operations no longer relate to the three fluorescence spectra considered individually, but to the concatenated spectra, i.e. arranged one after another in a single column (see FIG. 4).

The concatenated spectra can be subjected, according to the case, to:

a simple normalization by dividing each emission value of each concatenated spectrum by the standard of this same vector $X_i$. This normalization is applied to each sample (i=1 with I samples), that is:

$$x_{ij(standardized)} = \frac{x_{ij}}{\|x_{i.}\|}$$

in which j is the number of wavelengths of the concatenated emission spectrum (j=1 to 4545) and $$\|x_{i.}\| = \sqrt{\sum_j |x_{ij}|^2} \ ;$$

or a correction by "multiplicative scatter correction", which consists of performing a regression between the vector $x_j$ (the concatenated emission spectrum of each sample i) and the average concatenated vector of all of the samples (i=1 with I samples), then cancelling out the ordinate at the origin and dividing each intensity of the concatenated emission spectrum for each sample by the respective slope, as described below:

$$x_{i.} = a_i + b_i \bar{x}_{i.}$$

$$x_{ij}(MSC) = \frac{x_{ij} - a_i}{b_i}$$

In this regard, see [Bro 1998; Dhanoa 1994].

After having acquired and pre-processed the fluorescence spectra of a certain number of calibration samples, it is possible to determine the multi-way statistical model that will be used for the analysis of other samples to be characterized. This comprises the calculation of the "loading" vectors of this model.

First, the case of a multi-linear model of the "PARAFAC" type is considered [Bro 1998]. The principle, shown in FIG. 5, is to decompose a three-way structure (data cube) X into a sum of external three-vector products ("triads") $a_i$, $b_i$, $c_i$, plus a residue E, which is also in the form of a "data cube". The three ways constituting the "cube" X are: the samples, the excitation radiation and the emission wavelengths. It is therefore possible to write:

$$x_{ijk} = \sum_{f=1}^{F} a_{if} b_{jf} c_{kf} + \dot{e}_{ijk}$$

where: "i" is the index of the samples, "j" is that of the excitation radiation, "k" is that of the emission wavelengths, and "f" is that of the F PARAFAC decomposition factors.

The concatenation of the spectra makes it possible to write the PARAFAC decomposition in matrix form:

$$X_{I*JK} = A(C \otimes B)^T$$

where:

I, J and K are the numbers of samples, excitation wavelengths and emission wavelengths, respectively;

$X_{I*JK}$ is the matrix of concatenated fluorescences of all of the samples;

$B_{JK}$ and $C_{KF}$ are the excitation and emission "loading" vectors (with JF and KF elements, respectively) (bi-linear fluorescence profiles);

$A_{IF}$ is the "score" (or intensities of the spectral loadings) vector (with IF elements);

the symbol $\otimes$ represents the Khatri-Rao tensor product of; and the exponent T indicates the transpose of the column matrix.

The loading vectors are calculated on the basis of the calibration samples chosen so as to be representative of the total variability expected in the group of samples to be predicted subsequently. In other words, the model is empirical; it is therefore valid only for samples similar to those that were used for the calibration.

The parameters A, B and C of the PARAFAC model can be calculated by the method of alternating least squares (iterative non-linear method). In this method, a first estimation of the vector A is calculated conditionally on initial random values attributed to B and C in order to minimize the sum of the squares of the residues. The parameter B is then updated using the estimation of A, and then the parameter C is updated using the new value for B, and so on. Each iterative updating of A, B and C therefore improves the solution (reduction of the error surface). The algorithm converges when the improvement of the solution at the level of an iteration becomes very small (by default, this criterion is $10^{-6}$).

The convergence of the PARAFAC model for data that are weakly resolved and that, moreover, are not truly tri-linear, may be problematic [Bro 1998; Harshman 1984; Rizkallah 2007]. Indeed, the error surface of the model may contain local minima (points lower than in their vicinity, but higher than the true minimum of the surface), saddle points, flat terrains, and very narrow valleys that may slow or even prevent the convergence of the algorithm.

The present inventors have noted that, by imposing a limitation on the number of iterations (for example a maximum of 30 iterations) and/or by increasing the convergence criterion ($10^{-2}$ or $10^{-3}$ instead of $10^{-6}$), the model is significantly improved at the parameter level (loadings and scores), as will be shown below with the aid of FIG. 7. Indeed, an excessive number of iterations may degrade the relevance of the model.

The convergence may be facilitated by imposing a constraint of non-negativity since it is known a priori that the fluorescence spectra as well as their relative intensities cannot take negative values.

Finally, it has been noted that the pre-processing for removing the Rayleigh scattering by applying a GLZ model facilitates the convergence of the iterative method for calculating loading and score vectors of the PARAFAC model.

In the case of perfectly multi-linear data, the PARAFAC model in theory allows only a single solution. However, in the case of an EEM limited to 3 excitations, and when the fluorescence is collected at the surface, the tri-linearity of the EEM matrix is significantly disrupted.

Therefore, the solution is no longer unique and it is necessary to develop criteria for selecting the number of factors as well as the final model.

This choice is guided by a plurality of criteria known in themselves [Bro 1998; Harshman 1984]:
the verification of the conformity between the spectral parameters obtained (vectors B and C) and the a priori knowledge of the fluorophores present in the sample analyzed;
a criterion known by the name CORCONDIA [Bro 1998], which is used to verify the percentage of gap of the model with respect to a perfect multi-linearity model;
the study of the percentage of variance of the fluorescence data explained by the model;
the study of the structure of the residues, which must be random;
the study of the structure of the scores (vector A) in terms of coherence of the change in scores with respect to what is expected from the application of the transformation on the batch of calibration samples;
the repeatability and reproducibility of the scores, etc.

The scores thus obtained by the PARAFAC decomposition of the EEMs of the calibration samples are then used to construct a multiple regression (linear or generalized) on the content of the quality parameters to be measured. The coefficients of the regression as well as vectors B and C are stored in a database of the model.

The model is validated by applying it to new known samples for which the predicted values are compared to the values measured by the reference methods.

The EEMs obtained for new samples are pre-processed (removal of Rayleigh and standardization) in the same way as the EEMs of the calibration samples. The PARAFAC model and the regression model are applied to the new samples by using the stored coefficients (B, C and the regression coefficients) obtained from calibration samples. In the case of the use of an MSC-type normalization, the average spectrum of the calibration samples provides the reference for correcting the spectra of the new samples.

Starting with the cube of the pre-processed matrices of the new samples to be analyzed, the new scores are calculated on the basis of the "loading" vectors B and C, as follows:

$$A_{new} = (B \otimes C)^{+} * X_{new};$$

where the exponent + indicates the generalized inverse of the tensor product and $X_{new}$ indicates the concatenated and pre-processed spectral data of the new samples. The new scores are finally multiplied by the regression coefficients (obtained on the calibration samples) in order to obtain the quality parameters of the new samples.

Thus, the operations necessary for predicting the content of the quality parameters in the new samples to be analyzed consist of:
pre-processing the new spectra (removing the scattering and standardizing);
calculating the scores of the samples to be analyzed on the basis of the B and C vectors stored; and
applying the regression equation stored in order to obtain the content of the parameters.

The method described above was applied to predict the acrylamide content of the chicory samples (n=68).

For each sample, three spectra were acquired with excitations at 280, 340 and 429 nm, pre-processed by removing the scattering and standardization, and concatenated; then, the EEMs thus obtained were decomposed into four PARAFAC factors.

Figure 7:
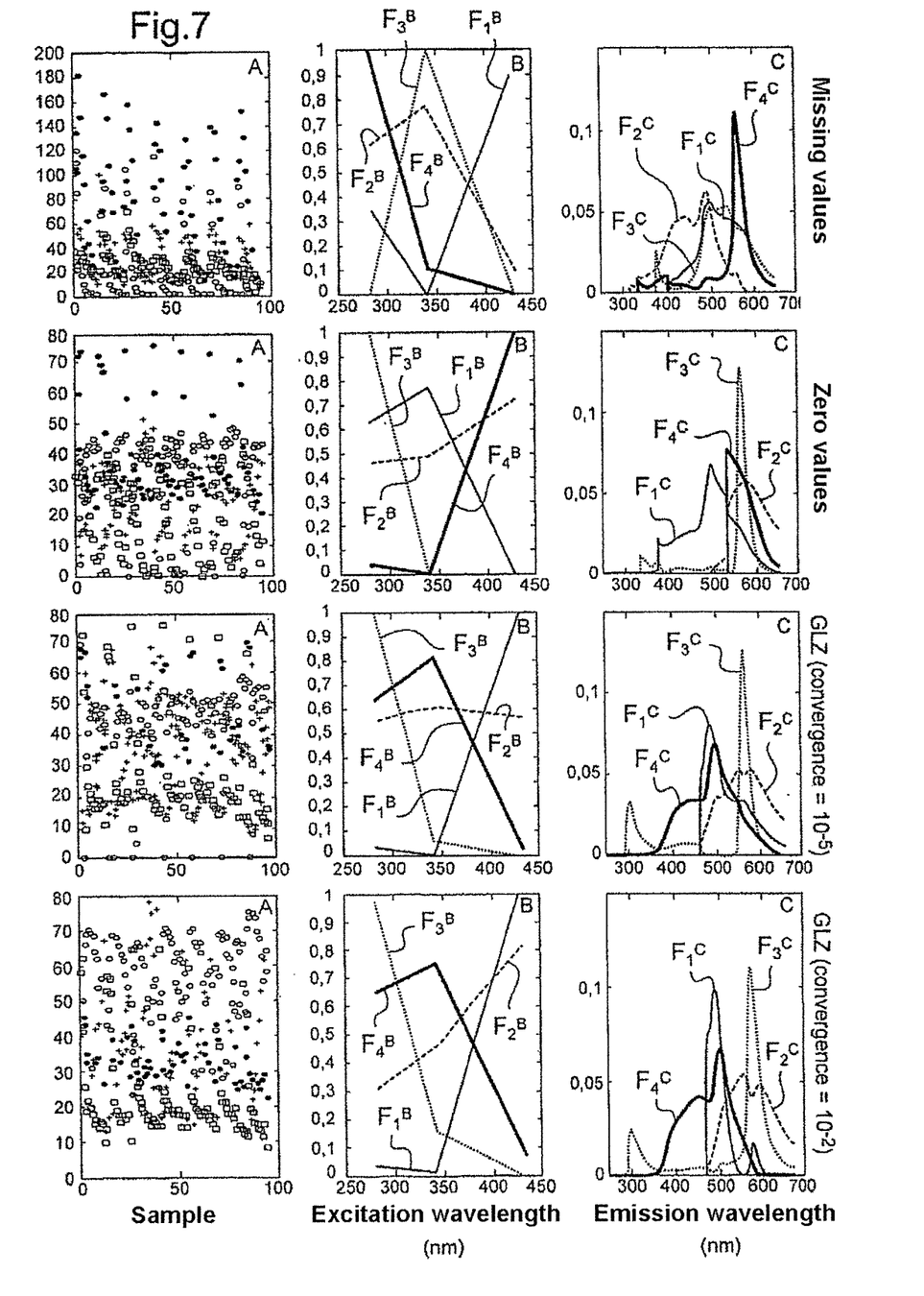
FIGS. 7 and 8: graphs showing the application of a method according to a first embodiment of the invention, based on a PARAFAC model, with prediction of the acrylamide content of different chicory samples.

In FIG. 7:
the graphs of the first column, called "A", represent the "scores" of the four PARAFAC factors (respectively, black points, gray circles, squares and stars) for 100 samples;
the graphs of the second column, called "B", represent the excitation "loadings" of the four PARAFAC factors (curves $F^B_1$, $F^B_2$, $F^B_3$, $F^B_4$) for these same 100 samples;
the graphs of the third column, called "C", represent the emission "loadings" of the four PARAFAC factors (curves $F^C_1$, $F^C_2$, $F^C_3$, $F^C_4$) for these same 100 samples.

The graphs of the first line relate to the case in which the Rayleigh scattering has been removed by introducing missing values; those of the third line relate to the case in which it has been removed by introducing zeros; those of the third and fourth lines relate to the case in which the removal of the Rayleigh scattering has been performed by using a generalized linear model.

With the exception of the data that include missing values, all of the other data has also been standardized by MSC.

The results show that the missing values at the level of the overlap of the scattering and the fluorescence (FIG. 7C, line 1) are poorly predicted, while the zeros produce artifacts (FIG. 7C, line 2) constituted by sudden variations in intensity. The models pre-processed with GLZ produce acceptable spectral parameters, with gradual variations in intensity (FIG. 7C, lines 3 and 4).

The convergence criterion of the model of FIG. 7, lines 1, 2 and 3 is $10^{-6}$ (criterion commonly used); that of the model of FIG. 7, line 4 is $10^{-2}$. The restriction imposed on the convergence of the model, either by limiting the number of iterations allowed and/or by increasing the convergence criterion, very significantly improves the model results in terms of structure of the scores (FIG. 7A, lines 3 and 4) and separation of factors (FIGS. 7B and C, lines 3 and 4). In particular, it the change in the curve $F^B_2$ may be noted, which, in the third line of the figure, shows a contribution of three excitation wavelengths; by contrast, in the fourth line, the separation of the excitations is clearly better. Similarly, the shoulder of the curve $F^C_1$ is considerably reduced when the convergence factor goes from $10^{-6}$ to $10^{-2}$.

Figure 8:
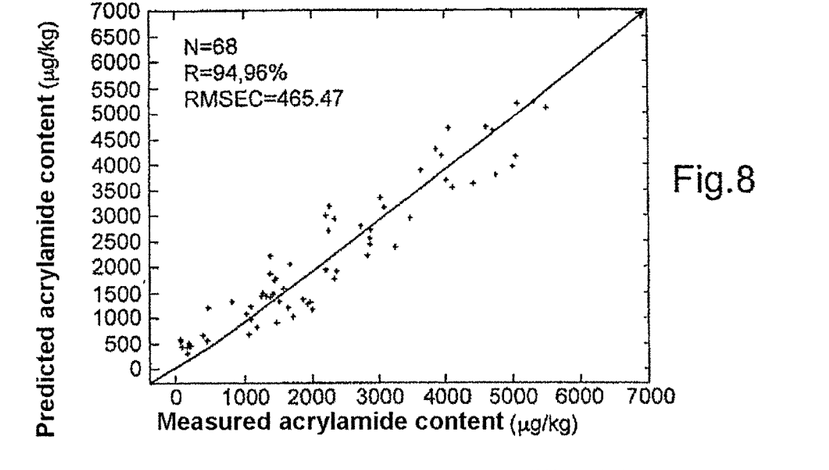

The scores resulting from the model shown in FIG. 7, line 4, were used to calibrate the acrylamide content chemically measured in the samples. The acrylamide content chemically measured and predicted by the model based on the PARAFAC scores of the fluorescence measured on the sensor are shown in FIG. 8. In this figure, the acrylamide content conventionally measured are reported on the x-axis, and those predicted by the model are on the y-axis. N is the number of samples, R is the correlation coefficient and the RMSEC is the square root of the average of the square of the errors. One may take note in particular of the high value of the correlation coefficient (almost 95%); the RMSEC is 465.47 µg/kg, i.e. around 15% of the average value of the acrylamide content measured.

When the regression resulting from the PARAFAC fluorescence scores does not lead to suitable results (for example, correlation coefficient R<0.85), another strategy that aims to improve the prediction of the regression model is applied. This method is based on NPLS multi-way regression, preferably coupled with a pre-processing operation by Orthogonal Signal Correction (OSC) [Wold 1998].

The OSC pre-processing aims to reduce or remove the variance contained in the fluorescence signal that is orthogonal to (not correlated with) the dependent variable (y) before performing the regression. The OSC is applied to the concatenated data after removing the scattering by the GLZ method and standardization pre-processing by MSC.

The algorithm most commonly used for the OSC correction is NIPALS ("non-linear iterative partial least squares"). The first step consists of extracting the vector of the scores t of the first main component (decomposition into singular values) and orthogonally projecting it onto the vector y: $t_{new}=(1-y(y^Ty)^{-1}y^T)t$. Then, an MLR- or a PLS-type regression (multivariate) is applied to predict the orthogonally projected vector: $w=X^+t_{new}$ (the convergence is tested on the new score $t^*=Xw$). When $t^*$ converges, the actual corresponding vector is calculated $p=XTt^*$ and the orthogonal effect is then removed from the fluorescence data ($X_{new}=X-t^*p^T$). In the application to the invention, a single OSC factor is calculated then removed before reorganization of the fluorescence data into a three-way structure. In the case of a single variable y, the model converges into a single iteration.

Unlike the PARAFAC decomposition model, the NPLS regression model [Bro 1998] searches for factors to explain both the fluorescence data $\underline{X}$ (three ways) and y (the dependent variable). The NPLS regression therefore searches for a decomposition of the data $\underline{X}$, which results in scores that have a maximum covariance with y; an internal regression between the NPLS scores of $\underline{X}$ and y then results in the calibration:

$$X^{(I \times JK)} = T(W^K \otimes W^J)^T + E_1$$

$$y = Tb + E_2$$

where T is the vector of the scores of X (having the best covariance with y) and the respective loading vectors for the excitations and emissions are $W^K$ and $W^J$.

The algorithm for the NPLS with f factors corresponding to data $\underline{X}$ (three ways) and a single dependent variable is described as follows:
1. Centering the data X and y and making $y_0 = y$
2. Beginning the iteration f=1
3. Calculating $Z = X^T y$
4. Determining $w^J$ and $w^K$ by decomposing z into singular values
5. Calculating the vectors t and arranging them in a matrix $T = [t_1\ t_2\ t_3\ t_f]$
6. Calculating the regression coefficients $b = (T^TT)^{-1}T^Ty_0$
7. Each sample $X_i$ is replaced by $X_i - t_i w^J (w^K)^T$ and $y = y_0 - Tb$
8. f=f+1. Restart phase 1 until y has been sufficiently explained.

(In these equations, the index of factor f has been omitted from t, $w^J$, $w^K$, and b).

Given that the NPLS is applied to the data after OSC pre-processing (therefore the major variance perpendicular to y has been removed), a single NPLS factor is used for the regression.

After concatenation of the EEMs from the new samples, the MSC pre-processing is applied by using the average spectrum of the calibration samples as a reference. The OSC factors (p and w) calculated on the calibration samples are then removed from the new samples:

$$X_c = X_n - X_n * w * (p^T * w)^{-1} * p^T$$

$X_n$ is the matrix of the EEMs concatenated and pre-processed by MSC and $X_c$ is the matrix of the concatenated EEMs corrected by OSC.

The loadings ($w^J$, $w^K$) and the regression coefficients b of the NPLS's obtained from the calibration samples are applied to the matrix $X_c$ to predict the scores of the new samples and their dependent variable.

$$T_n = (W^J \otimes W^K)^+ * X_c$$

$$\hat{y} = T_n b + e.$$

The NPLS method was applied to the prediction of the vitamin C content of the green bean samples.

FIGS. 9A, 9B, 10A and 10B are graphs showing the application of a method according to a second embodiment of the invention, based on an NPLS model, to the prediction of the vitamin C content of different green bean samples.

Figure 9A:
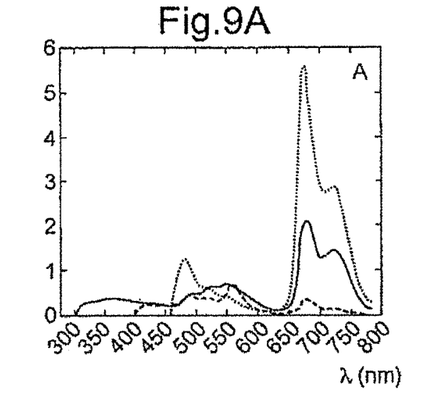
FIGS. 9A, 9B, 10A and 10B: graphs showing the application of a method according to a second embodiment of the invention, based on an NPLS model, with prediction of the vitamin C content of different green been samples.
Figure 9B:
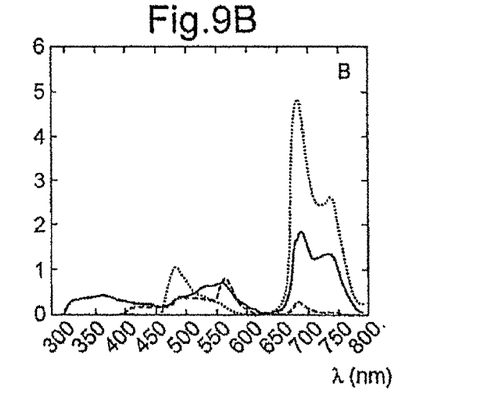

After acquisition of the EEM matrices of n=60 green bean samples (FIG. 9A: raw spectra), removal of the scattering (GLZ model) and standardization by MSC, an OSC factor was applied to remove, from the fluorescence data, the major portion of the variance orthogonal (non-explicative) to the dependent variable (chemically measured vitamin C content): see FIG. 9B, pre-processed spectra.

Then, an NPLS model with a factor was applied to calibrate the "cube" of the EEMs pre-processed on the chemically measured vitamin C content.

Figures 10A, 10B:
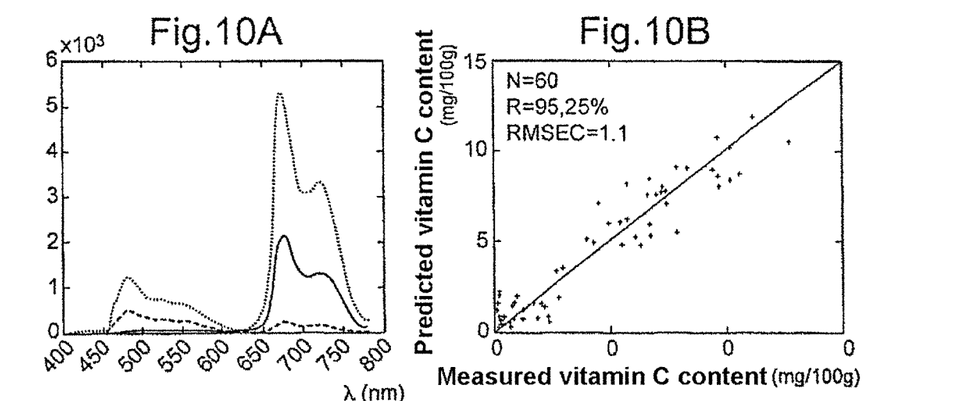

FIG. 10A shows the NPLS regression coefficients for the three emission spectra (excitation at 280 nm: black line; excitation at 340 nm: gray line; excitation at 429 nm: dotted line). FIG. 10B shows a graph of the vitamin C content conventionally measured (x-axis) and predicted by applying the NPLS model to three self-fluorescence spectra (y-axis). N is the number of samples, R is the correlation coefficient and RMSEC is the square root of the average of the squares of the errors. Again, one may take note of the very high value of the correlation coefficient (above 95%) and the fact that the average quadratic error RMSEC is on the order of 15%, which is acceptable for the applications considered here.

The invention has been described in reference to two particular examples in which it was applied to the determination of the concentration in food samples of a substance of interest. The invention is not, however, limited to this type of application. More generally, it can make it possible to determine various quality indicators of a sample; these indicators may be chemical, as in the aforementioned examples, but also microbiological (microbial load), physicochemical or chemical. The invention also makes it possible to characterize the methods to which the samples are subjected, by providing estimations of parameters such as the sterilizing or pasteurizing value, the time-temperature product or the cooking value of a heat treatment method.

REFERENCES

[Bro 1998] Bro, R. "Multi-way Analysis in the Food Industry Models, Algorithms, and Applications", PhD thesis, Universiteit van Amsterdam, 1998.

[Dhanoa 1994] Dhanoa, M. S.; Lister, S. J.; Sanderson, R.; Barnes, R. J. "The link between multiplicative scatter correction (MSC) and standard normal variate (SNV) transformations of NIR spectra." J. Near Infrared Spectrosc. 1994, 2, 43-47.

[Harshman 1984] Harshman, R. A. "How can I know if it's real?" A catalog of diagnostics to use with three-mode factor analysis and multidimensional scaling." In: Research methods for multimode data analysis. Law, H. G.; Snyder, C. W.; Hattie, J. A.; McDonald, R. P., eds. pp. 566-571, Praeger, N.Y., 1984.

[Rizkallah 2007] Rizkallah, J. "Chemometric Analysis of Front Face Fluorescence Data—Estimation, of Neoformed Contaminants in Processed Foods." PhD thesis, Agro Paris Tech France, 2007.

[Wold 1998] Wold, S.; Antti, H.; Lindgren, F.; Ohman. "Orthogonal signal correction of near-infrared spectra." Chemometr. Intell. Lab. Syst. 1998, 44, 175-185.

[Nahorniak 2003] Nahorniak Michelle L, Booksh Karl S. "Optimizing the implementation of the PARAFAC method for near-real time calibration of excitation-emission fluorescence analysis" J. Chemometrics 2003; 17; 608-617.

[Rizkallah et al., 2008] Rizkallah J., Lakhal L., Birlouez-Aragon I.: "Front face fluorescence to monitor food processing and neoformed contamination" In "Optical Methods for Monitoring Fresh and Processed Food—Basics and Applications for a better Understanding of Non-Destructive Sensing" Chapter 4. Editor Zude M. Publisher, CRC Press, USA (2008)

[Davidson 1998] Davidson, R.; MacKinnon J. G. "Econometric theory and methods. Generalized least squares and related methods" in "Econometric Theory and Methods", Oxford University Press 2004, pp 255-261.

The invention claimed is:

1. Method for spectroscopic analysis of at least one sample implementing a method for analysis of spectroscopic data based on a multi-way statistical model, which method includes:
   a) the illumination of said or of each sample to be analyzed by a plurality of excitation light radiations with respective wavelengths;
   b) the acquisition of front-face fluorescence spectra of said or of each sample, each corresponding to a respective excitation light radiation;
   c) a pre-processing of the fluorescence spectra acquired;
   d) for each sample, the calculation of a score vector by application to the pre-processed spectra of said multiway statistical model, identified by a fluorescence excitation loading vector and by an emission loading vector; and
   e) the determination of at least one parameter chosen from a quality indicator of said or of each sample and a parameter characterizing a method to which said or each sample has been subjected, on the basis of said score vector;
   the method being characterized in that the average spectral gap between said excitation light radiation is at least 50 nm over a spectral range of at least 100 nm.

2. Method according to claim 1, in which the number of excitation light radiations and corresponding fluorescence spectra for each sample is between two and six, over a spectral range of at least 100 nm.

3. Method according to claim 1, also including a preliminary calibration phase comprising:
   i) the illumination of a plurality of calibration samples by said excitation light radiation;
   ii) the acquisition of front-face fluorescence spectra of the samples, corresponding to said excitation light radiation;
   iii) a pre-processing of the acquired fluorescence spectra;
   iv) the determination, by an iterative method, of said loading excitation and emission vectors of the multi-way model, as well as a score vector for each calibration sample; and
   v) the determination of a regression function linking said scores to the known values of said or of each parameter for said calibration samples.

4. Method according to claim 1, in which the fluorescence spectra are pre-processed by subtracting a contribution due to the first-order Rayleigh scattering of the excitation light radiation, with said contribution being calculated by means of a generalized linear model.

5. Method according to claim 4, in which said generalized linear model is determined on the basis of a first portion (RD) of the spectrum to be pre-processed, including only said contribution due to the Rayleigh scattering, and is used to predict the Rayleigh scattering contribution in a second portion (RP) of said spectrum in which it is superimposed with a fluorescence contribution.

6. Method according to claim 1, in which the fluorescence spectra are pre-processed by being normalized.

7. Method according to claim 1, in which the fluorescence spectra of a plurality of samples, for calibration and/or to be analyzed, are pre-processed by performing a multiplicative scatter correction.

8. Method according to claim 1, in which said multi-way statistical model is a PARAFAC model, with the fluorescence spectra of each sample being represented in concatenated form.

9. Method according to claim 8, in which the loading vectors of said PARAFAC model are determined by an iterative method that is stopped when the reduction of the loss function due to the last iteration goes below a threshold value between $10^{-4}$ and $10^{-2}$.

10. Method according to claim 1, in which said multi-way statistical model is an NPLS model, with the fluorescence spectra of each sample being represented in concatenated form.

11. Method according to claim 10, in which the fluorescence spectra are pre-processed by orthogonal signal correction.

12. Method according to claim 1, in which said excitation light radiation includes:
   a first radiation with a wavelength of between 270 and 300 nm;
   a second radiation with a wavelength of between 300 and 360 nm; and
   a third radiation with a wavelength of between 400 and 500 nm.

13. Method according to claim 1, in which said or at least one said parameter to be determined is chosen from:
   the content of a substance of interest in said or in each sample;
   a microbial load of said or of each sample; and
   a sterilizing, pasteurizing or cooking value, or a time-temperature product, of a method to which said or each sample has been subjected.

14. Method according to claim 1, in which the samples to be analyzed and for calibration are samples of a product chosen from: a food and a drug.

15. Use of a method according to claim 14 to measure the change in nutritional, microbiological and/or toxicological properties of a food during its preparation or preservation.

16. Appliance for spectroscopic analysis of at least one sample comprising:
   a set of light sources for illuminating said or each sample to be analyzed by respective excitation light radiations, having different wavelengths with an average spectral gap of at least 50 nm over a spectral range of at least 100 nm;
   means for acquisition (M, D) of the front-face fluorescence spectra emitted by said or each sample when illuminated by said excitation light radiation; and means for processing the fluorescence spectra acquired, suitable for implementing a method according to claim 1.

17. Appliance for spectroscopic analysis according to claim 16, comprising between two and six of said light sources.

18. Appliance according to claim 17, comprising:
a first light source emitting radiation at a wavelength of between 270 and 300 nm;
a second light source emitting radiation at a wavelength of between 300 and 360 nm; and
a third light source emitting radiation at a wavelength of between 400 and 500 nm.

* * * * *